United States Patent [19]

Nanba et al.

[11] Patent Number: 5,962,279

[45] Date of Patent: *Oct. 5, 1999

[54] PROCESS FOR PRODUCING D-AMINO ACIDS WITH COMPOSITE IMMOBILIZED ENZYME PREPARATION

[75] Inventors: Hirokazu Nanba; Yukio Yamada, both of Kakogawa; Kazuyoshi Yajima, Akashi; Masayuki Takano, Kakogawa; Yasuhiro Ikenaka, Akashi; Satomi Takahashi; Takehisa Ohashi, both of Kobe, all of Japan

[73] Assignee: Kanegafuchi Kagaku Kogyo Kabushiki Kaisha, Oaska, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/596,144

[22] PCT Filed: Jun. 23, 1995

[86] PCT No.: PCT/JP95/01257

§ 371 Date: Aug. 16, 1996

§ 102(e) Date: Aug. 16, 1996

[87] PCT Pub. No.: WO96/00296

PCT Pub. Date: Jan. 4, 1996

[30] Foreign Application Priority Data

Jun. 24, 1994 [JP] Japan ..................................... 6-142977

[51] Int. Cl.$^6$ .............................. C12P 13/04; C12N 11/00
[52] U.S. Cl. ...................... 435/106; 435/174; 435/176; 435/175; 435/177; 435/178; 435/179; 435/180; 435/188; 435/195; 435/280
[58] Field of Search ..................................... 435/106, 176, 435/178, 180, 188, 280, 320.1, 252.1, 252.2, 252.3, 252.31, 252.33, 252.5, 174, 175, 177, 179; 530/23.2

[56] References Cited

U.S. PATENT DOCUMENTS

| 4,065,353 | 12/1977 | Cecere et al. ................................. 195/2 |
| 4,211,840 | 7/1980 | Nakamori et al. ....................... 435/107 |
| 4,248,967 | 2/1981 | Viglia et al. ............................. 435/106 |
| 4,312,948 | 1/1982 | Olivieri et al. .......................... 435/253 |
| 4,418,146 | 11/1983 | Lungershausen et al. .............. 435/106 |
| 5,283,182 | 2/1994 | Powell et al. ............................ 435/106 |

FOREIGN PATENT DOCUMENTS

| 0677584 A1 | 10/1995 | European Pat. Off. . |
| WO 94/03613 | 2/1994 | WIPO . |
| WO 94/08030 | 4/1994 | WIPO . |

OTHER PUBLICATIONS

Lee et al. "Isolation of thermostable D–hydantoinase–producing . . . " Biotech. Lett. 16(5), 461–466, May 1994.

Fersht, A. "Enzyme Structure and Mechanism" second edition, W. H. Freeman and Com., Chapter 5, pp. 155–168, 1977.

Primary Examiner—Robert A. Wax
Assistant Examiner—Nashaat T. Nashed
Attorney, Agent, or Firm—Foley & Lardner

[57] ABSTRACT

A process for the efficient production of a D-amino acid from the corresponding DL-5-substituted hydantoin by one-step reaction which comprises using a composite immobilized enzyme at a pH about neutrality, said composite immobilized enzyme being obtained by immobilizing a hydantoinase having its optimal pH within an alkaline range and a D-N-carbamyl-α-amino acid amidohydrolase having its optimal pH about neutrality in a coexisting state on an immobilizing support, simultaneously, is disclosed.

12 Claims, 3 Drawing Sheets

PROCESS FOR PRODUCING D-AMINO ACIDS WITH COMPOSITE IMMOBILIZED ENZYME PREPARATION

This is a continuation of U.S. national stage application of PCT/JP95/01257 filed Jun. 23, 1995.

FIELD OF THE INVENTION

The present invention relates to a composite immobilized enzyme preparation and a process for producing D-amino acids using the preparation. In particular, the composite immobilized enzyme preparation of the present invention is useful for the production of D-α-amino acids which are intermediate compounds for the production of antibiotics, such as D-(p-hydroxyphenyl)glycine to be used for the production of the antibiotic, amoxycillin and the like.

BACKGROUND OF THE INVENTION

Optically-active D-amino acids are important compounds as intermediate compounds for drugs and it has been known that they can be produced efficiently by combining an asymmetric hydrolysis reaction of 5-substituted hydantoins into the corresponding D-N-carbamyl-α-amino acids with the enzymes, hydantoinases (hereinafter sometimes abbreviated as "Hase") (JP-B 62-30785), and an conversion reaction of the resultant D-N-carbamyl-a-amino acids into the corresponding D-α-amino acids with the enzymes, D-N-carbamyl-α-amino acid α-midohydrolases (hereinafter sometimes abbreviated as "decarbamylase" or "DCase") (PCT/JP91/01696: WO 92/10579).

In addition, JP-A 63-185382, WO 92/00739 and the like disclose that the respective reactions are carried out more efficiently by using these enzymes in the form of so-called immobilized enzymes wherein they are immobilized on supports such as ion exchange resins and the like.

However, a two-step reaction has been employed for carrying out these reactions because the optimal and stable pH's of both enzymes are considerably different from each other. Therefore, both immobilized enzymes should be prepared separately and complicated reaction operations are required.

OBJECTS OF THE INVENTION

The present invention relates to a technique for producing D-α-amino acids efficiently by using an immobilized enzyme resin obtained by immobilizing both hydantoinase and decarbamylase on one immobilizing resin support in a coexisting state of the enzymes (hereinafter referred to as a "composite enzyme"), simultaneously.

In these two enzymatic reactions for converting 5-substituted hydantoins into D-α-amino acids, in general, the optimal pH of the hydantoinase reaction is pH 8 to 9 and the solubility of the substrate is increased as increase in pH. In addition, the racemic reaction of the hydantoin ring is promoted in an alkaline range. Therefore, it is desired to carry out the hydantoinase reaction in the pH ranging from 7 to 10, preferably in an alkaline range. On the other hand, in general, the optimal pH of the decarbamylase reaction is pH 6.5 to 9.0 but the hindrance of the reaction by ammonia formed is remarkably increased as increase in pH. Therefore, it is desired to carry out the decarbamylase reaction at pH about neutrality.

If so-called one-step reaction can be employed for carrying out these reactions, i.e., these two enzymatic reactions can be carried out in one reaction vessel simultaneously, in comparison with so-called two-step reaction wherein two different enzymes react with the substrates separately, reaction operations become simple and the overall reaction time can be shortened. In addition, by combining the hydantoinase reaction which is a reversible reaction and the decarbamylase reaction which is a irreversible reaction, the conversion yield of hydantoin can be improved as well as the subsequent purification of D-amino acids can be simplified. Thus, it is expected to significantly reduce the production cost. However, when the respective enzymes are immobilized on different immobilizing supports and they are mixed upon using them, the reactivities become inferior because of the difference in optimal pH and there is a problem in the stability of the immobilized enzymes.

The present inventors have intensively studied to produce a composite immobilized enzyme preparation wherein both enzymes are immobilized on one immobilizing support simultaneously. If these two enzymes are immobilized simultaneously, two enzymatic reactions occur successively in micro-spaces of resins. Therefore, movement of the substrate for a decarbamylase, a D-N-carbamyl-α-amino acid, from immobilized Hase to immobilized DCase by diffusion is not required and pH variation in the micro-spaces can be minimized. Thus, it is expected that, in addition to increase in reactivities of the respective enzymes and relief of the product hindrance due to ammonia, stability of enzymes upon using repeatedly is improved.

SUMMARY OF THE INVENTION

The present invention provides a process for the efficient production of a D-amino acid from the corresponding DL-5-substituted hydantoin by one-step reaction which comprises using a composite immobilized enzyme at a pH about neutrality, said composite immobilized enzyme being obtained by immobilizing a hydantoinase having its optimal pH within an alkaline range and a D-N-carbamyl-α-amino acid amidohydrolase having its optimal pH about neutrality in a coexisting state on an immobilizing support of an anionic ion exchange resin, simultaneously (hereinafter referred to as composite enzyme).

DETAILED EXPLANATION OF THE INVENTION

Figure 1:
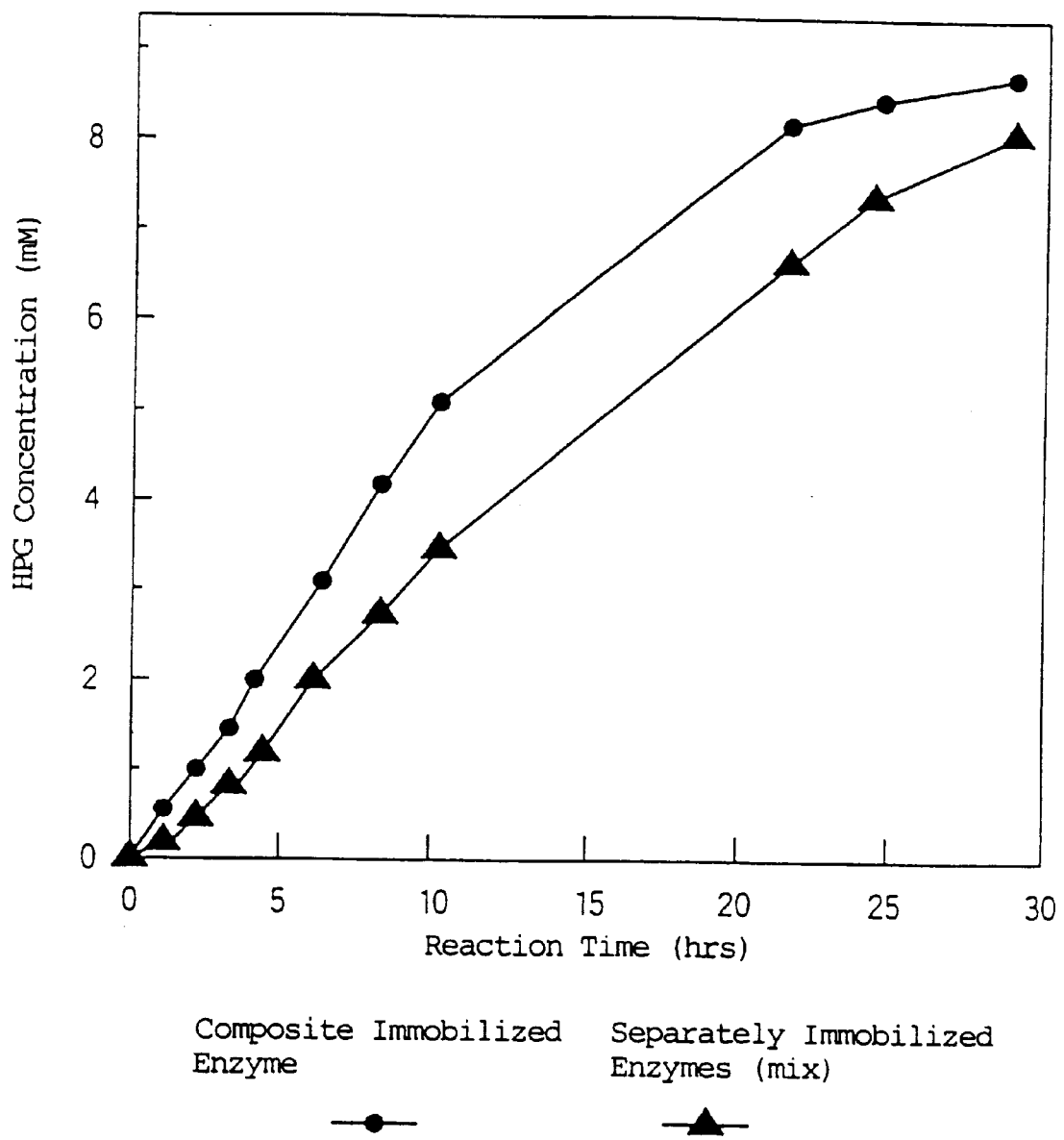
FIG. 1 is a graph illustrating the time courses of the reactions for the production of the corresponding D-p-hydroxyphenylglycine from 5-(p-hydroxyphenyl)hydantoin in Example 3 by using the composite immobilized enzyme preparation of the present invention and the mixture prepared by immobilizing hydantoinase and decarbamylase separately to the different resins.

As for the hydantoinase used in the present invention, the enzymes from animals, plants and microorganisms can be used. The hydantoinases from microorganisms are suitable for industrial production. As such a microorganism, those disclosed in JP-B 62-30758 are exemplified. The bacteria include Achromobacter, Aerobacter, Aeromonas, Aqrobacterium, Alcaliqenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sarcina, Serratia, Xanthomonas and the like. The Actinomycetes include Actinomyces, Mycobacterium, Nocardia, Streptomyces, Actinoplanes and the like. The filamentous fungi include Asperqillus, Paecilomyces, and Penicillium and the like. The yeasts include Candida, Pichia, Rhodotorula, Torulopsis and the like.

Among the above microorganisms, examples of strains which have relatively high hydantoinase activities and are excellent in practical use include *Aerobacter cloacae* IAM 1221, Agrobacterium rhizogenes IFO 13259, *Brevibacterium incertum* IFO 12145, *Corynebacterium sepedonicum* IFO 3306, *Microbacterium flavum* ATCC 10340, *Micrococcus roseus* IFO 3764, *Pseudomonas striata* IFO 12996, *Mycobacterium smecmatis* ATCC 607, *Nocardia corallina* IFO 3338, *Streptomyces flaveolus* IFO 3241, Bacillus sp. KNK108 (FERM P-6056), Bacillus sp. KNK245 (FERM BP-4863) and the like.

In addition, the enzymes produced by artificial microorganisms in which hydantoinase productivity is imparted or increased by gene recombinant technique, for example, *E. coli* HB101pTH104 (FERM BP-4864), or the dihydropyrimidinase having similar activity as disclosed in JP-A 53-136583 can be used.

As for the decarbamylase used in the present invention, the origins thereof is not specifically limited and those derived from animals, plants and microorganism can be used. However, for industrial production, the enzymes from microorganisms are suitable. Examples of such microorganisms include naturally occurring microorganisms such as Agrobacterium Pseudomonas, Arthrobacter, Alcaligenes, Achromobacter, Moraxella, Paracoccus, Aerobacter, Aeromonas, Brevibacterium, Bacillus, Flavobacterium and Serratia disclosed in JP-B 57-18793, JP-B 63-20520 and JP-B 1-48758, or the artificial microorganisms described in WO 91/01696 in which decarbamylase productivity is imparted or increased by gene recombinant technique. Representative examples of such microorganisms include Agrobacterium sp. KNK712 (FERM BP-1900), Pseudomonas sp. KNK003A (FERM BP-3181), Pseudomonas sp. KNK505 (FERM BP-3182), *Escherichia coli* JM109pAD108 (FERM BP-3184), *E. coli* JM109pPD304 (FERM BP-3183) and the like.

When a stabilized decarbamylase in which the amino acid responsible for heat resistance of the decarbamylase is replaced by another one is used, the following transformants disclosed in WO 94/03613 can be used. For example, the transformants include *E. coli* JM109pAD402 (FERM BP-3912), *E. coli* JM109pAD404 (FERM BP-3913), *E. coli* JM109pAD406 (FERM BP-3914), *E. coli* JM109pAD416 (FERM BP-3915), *E. coli* JM109pAD428, *E. coli* JM109pAD429 (FERM BP-4035), *E. coli* JM109pAD431, *E. coli* JM109pAD434, *E. coli* JM109pAD435, *E. coli* JM109pAD439, *E. coli* JM109pAD441, *E. coli* JM109pAD445, *E. coli* JM109pAD447, *E. coli* JM109pAD448, *E. coli* JM109pAD450, *E. coli* JM109pAD421, *E. coli* JM109pAD422, *E. coli* JM109pAD423, *E. coli* JM109pAD424 (FERM BP-4034), *E. coli* JM109pAD425, *E. coli* JM109pAD426, *E. coli* JM109pAD427, *E. coli* JM109pAD451, *E. coli* JM109pAD452, *E. coli* JM109pAD453, *E. coli* JM109pAD461, *E. coli* JM109pAD454, *E. coli* JM109pAD455 (FERM BP-4036), *E. coli* JM109pAD456, *E. coli* JM109pAD468, *E. coli* JM109pAD469, *E. coli* JM109pAD470, *E. coli* HB101pNT4553 (FERM BP-4368) or the like. When such stabilized enzymes are used, better results can be obtained in repeated use of the composite immobilized enzyme preparation of the present invention.

The enzymes used in the present invention can be produced simultaneously by using a microorganism which is capable of producing both enzymes. Alternatively, the enzymes can be produced separately or simultaneously using microorganisms which are capable of producing respective enzymes alone. As the microorganism which is capable of producing both enzymes, a microorganism isolated from a natural source such as an Aqrobacterium disclosed in JP-B 63-250520 and the like can be used. In addition, a recombinant microorganism prepared by isolating genes of both enzymes from the microorganisms isolated from a natural source and introducing them into a host, for example, the microorganisms disclosed in WO 94/00577, can be used. Alternatively, genes of both enzymes can be isolated from the same or different microorganisms and inserted into the same vector in the expressible form of both genes, or inserted into different vectors having different replication modes, for example, pUC19 and pACYC184. Then, the recipient host such as *E. coli* can be transformed with the above vector or vectors so that a single microorganism can produce both enzymes. In these cases, by selecting the kinds of promoters having various capabilities and the plasmids having different copy numbers, the ratio of production of each enzyme can be varied according to a particular purpose. However, it is preferred to adjust the ratio so as to obtain almost equal amounts of enzyme proteins. In the case that microorganisms which produce different enzymes separately are used, strains isolated from natural sources or recombinant microorganisms prepared by using gene recombinant technique can also be used. In such case, the production of the enzymes can be carried out either by cultivating the producer microorganisms separately, or cultivating in a mixed culture at various ratios, preferably, at such a ratio that almost equal amounts of the enzymes can be produced.

The cultivation can be carried out aerobically, for example, by shaking culture using flasks or by spinner culture with aeration. As for culture medium used in the cultivation, normally, an nutrient medium which contains generally used natural nutrients such as meat extract and polypeptone and the like can be used. When hydantoinase is produced separately or simultaneously with decarbamylase, a good result can be obtained by carrying out the cultivation with addition of manganese ion in an amount of, for example, as manganese chloride, 1 to 100 mg/liter, preferably about 20 mg/liter.

In the present invention, the enzymes can exist in the immobilized enzyme preparation in the purified, partially purified or crude form, or in some cases, in the form of microbial cells per se. And, in so far as the enzymes are under the conditions that the enzymatic activities can be exhibited the enzymes can exist in any form, and can be accompanied by any substance.

In the preparation or use of the composite immobilized enzyme preparation of the present invention, better results can be obtained by adding an antioxidant for a repeated use. As such an antioxidant, there can be used dithiothreitol, 2-mercaptoethanol, L-cystein hydrochloride, cysteamine hydrochloride, dithioerythritol, a mixture of dithiothreitol and dithioerythritol, reduced glutathione and the like.

An immobilized support used can be varied according to particular use conditions of the immobilized enzymes. When a crude enzyme solution such as a cell-free extract, or a partially purified enzyme solution treated by ammonium sulfate precipitation or the like are subjected to immobilization, polymer supports having ion exchanging groups or covalent bonding groups can be used.

As for a polymer support having an ion exchanging group, for example, Duolite A (registered trade mark) series, or Amberlite IRA (registered trade mark) series, the exchanging groups of which are primary, secondary, tertiary and quaternary amines; or a polystyrene resin having a diethanol type functional group, for example, Diaion EX can be used.

As for a support with a covalent bonding group, a substituted polymethacrylate polymer having an aldehyde as a bonding group, a high density alumina covered with a complex of polyethyleneimine/glutaraldehyde and the like can be used.

To immobilize whole microbial cells such as live cells or dried cells, a polymer such as polyacrylamide, polyurethane or calcium alginate, or a porous material such as alumina can be used.

The composite immobilized enzyme preparation of the present invention is produced as follows. A solution of the crude composite enzyme in which activities of Hase and DCase are appropriately adjusted is contacted with a support to adsorb the respective enzymes and treated with a cross-linking agent for stabilization. To prepare a solution of the crude composite enzyme, firstly, each enzyme is produced by cultivating microbial cells. In this case, a cell-free extract can be prepared by collecting the cells and disrupting them with, for example, sonication, mechanical disruption (for example, homogenizer) or enzyme treatment, when a microorganism capable of producing the enzymes simultaneously is used. When a solution of the composite enzyme is prepared by using different microorganisms, it can be prepared by cultivating the microorganisms separately, collecting the cells, preparing respective cell-free extracts and mixing them. Or, it can be prepared by cultivating respective producer microorganisms together and disrupting the cells at the same time to prepare a cell-free extract in which both two enzymes are mixed. When both enzymes are produced by different microorganisms, the productivities vary to a large extent according to the kinds of the microorganisms and difference in the cultivation methods. However, in general, regarding hydantoinase, a normal producer microorganism produces hydantoinase at about 0.1 to about 10 units/ml (one unit of the enzyme used herein is defined as an amount required to convert the substrate 5-(p-hydroxyphenyl)hydantoin into D-N-carbamyl-p-hydroxyphenylglycine at pH 8.7, 40° C., for 1 min) and a recombinant artificial producer microorganism produces it at about 5 to about 150 units/ml. Regarding decarbamylase, a normal producer microorganism produces decarbamylase at about 0.01 to about 2 units/ml (one unit of the enzyme used herein is defined as an amount required to convert the substrate D-N-carbamyl-p-hydroxyphenylglycine into D-p-hydroxyphenylglycine at pH 7.0, 40° C., for 1 min) and a recombinant artificial producer microorganism produces it at about 0.1 to about 20 units/ml. The ratios of Hase and DCase activities in a solution of the crude composite enzyme are adjusted so that the reaction producing D-α-amino acid from 5-substituted hydantoin can proceed most efficiently. As described hereinafter, this reaction is carried out at a pH of neutrality which is near the optimal pH for DCase and therefore the conditions are different from those for exhibiting maximal activity of Hase. Then, it is desired that both enzymatic activities are adjusted so that almost equal activities are exhibited at the reaction pH. For example, in the case of carrying out the reaction at pH 7.5, the desired composite immobilized enzyme preparation can be produced by carrying out the immobilization reaction using an enzyme solution in which there are almost equal amounts of proteins and enzymatic activities so that hydantoinase is about five times as much as the DCase in units. To maintain such activities after immobilization, it is desired that the ratio of the enzyme activities (Hase: DCase) in a solution of the crude composite enzyme should be in a range of 1 to 10:1. Therefore, after disruption of the microbial cells and before adsorption, the activities of the crude composite enzyme are adjusted to such levels.

In addition, to adsorb appropriate amounts of enzymes on the support, it is preferred to adjust the concentration of decarbamylase in the solution of the crude composite enzyme to 10 to 300 units/ml. The activity adsorbed is about 20 to about 90% of the activity added and no substantial difference can be seen between both enzymes.

The support is used after activation of its exchanging group with, for example, aqueous solution of sodium chloride and equilibrating, for example, in a buffer solution. It is preferred that the ratio of the solution of the crude composite enzyme and the support is adjusted so that the total amount of the protein in the crude enzyme solution are almost the same as the maximum adsorption capacity of the support. If necessary, 1 to 10 mM of an antioxidant and/or 0.5 to 20 mM of manganese ion can be present. The mixture is stirred at 4 to 30° C., preferably at 15° C., and the support is collected by filtration after the amount of enzyme adsorbed reaches the given amount (normally 8 to 48 hours, preferably this is carried out under the atmosphere of inert gas, such as nitrogen). Then, the support is washed and insolubilized by treating with a cross-linking agent to stabilize it. As for a cross-linking agent, a known agent such as at less than 1%, preferably 0.1 to 0.2% glutaraldehyde can be used. The cross-linked composite enzyme immobilized preparation is washed with distilled water and a buffer solution (preferably containing 0.1 to 20 mM, normally 1 to 5 mM antioxidant as described above) and stored in wet state in a sealed vessel at a low temperature (4° C.). In general, the activities of the composite immobilized enzyme preparation thus obtained are 5 to 80 units/g support with respect to decarbamylase. For hydantoinase, its activity is 1 to 10 times as much as the decarbamylase activity according to the adsorption conditions.

The process for producing D-a-amino acids from 5-substituted hydantoins by using the composite immobilized enzyme preparation of the present invention will be described hereinafter.

The reaction is carried out by reacting the substrate, 5-substituted hydantoin, with the composite immobilized enzyme preparation, if necessary, in the presence of an antioxidant agent and/or manganese ion. Normally, it is preferred that the reaction is carried out in the presence of 0.1 to 20 mM of an antioxidant agent and manganese ion. The reaction proceeds according to the following reaction scheme:

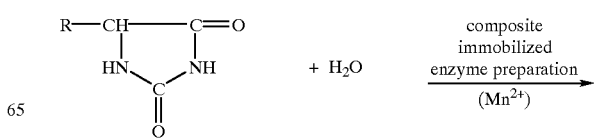

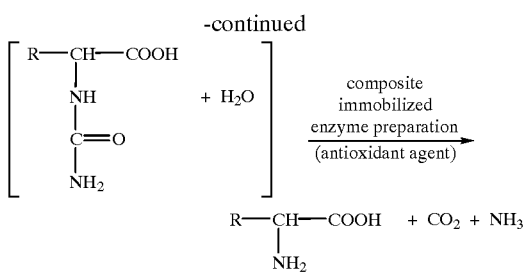

wherein R represents phenyl group, phenyl group substituted with hydroxy group, alkyl group, substituted alkyl group, aralkyl group or thienyl group.

The concentration of the substrate 5-substituted hydantoin to be used is 0.1 to 30% (w/v), preferably 1 to 5% (w/v). It is preferred that the amount of the composite immobilized enzyme preparation to be used is about 10 to about 20 units/g substrate as decarbamylase activity. The reaction temperature varies according to particular enzymes but, in general, it is 30 to 60° C. Enzymes having heat resistance be used at much higher temperature.

The reaction pH is suitably selected from the range of 6.5 to 8.0. The pH range is almost optimal for DCase. However, it is considerably far from the optimal pH for Hase and the Hase activity decreases several times as low as the activity at the optimal pH. The rate of racemization also decreases. However, ultimately, the production of D-α-amino acid is governed by the enzyme of the last step, DCase, it is preferred to set the amount of the enzyme and the reaction conditions based on the DCase (i.e., the optimal conditions for DCase) and to combine Hase activity in proportion to that DCase activity. In general, the ratio of the enzymes to be adsorbed to the support is adjusted so that almost equal activities can be expressed, although this varies according to particular reaction conditions. The "almost equal activities" mean the situation where the ratio of the hydantoinase activity measured at pH 7.5 (represented in "units (pH 7.5)"), and the decarbamylase activity as described above is about 0.5 to 1.5:1. The reaction is carried out with adjusting a reaction pH to the pH range thus selected, normally to pH 7.5. By these operations, the unfavorable conditions for Hase are overcome and the reaction equilibrium is declined toward the production of D-N-carbamyl amino acid. Thus, the reaction can be carried out more efficiently than expected and the conversion of the substrate, a 5-substituted hydantoin, can be improved. When the reaction is carried out at an alkaline pH range near the optimal pH of hydantoinase, the decarbamylase activity decreases to below the half of the activity at the optimal pH, though the production of a D-N-carbamyl amino acid can proceed successfully. In addition, it has been observed that the whole yield decreases and that the stability of decarbamylase itself is lowered because the reaction is largely inhibited by ammonia produced by the reaction. For these reasons, the reaction using the composite immobilized enzyme preparation can be carried out efficiently when the composite immobilized enzyme preparation having such immobilization ratio that the decarbamylase reaction is slightly rate-determining is used under conditions near the optimal reaction conditions and the substrate concentration of decarbamylase. In addition, it is advantageous that the whole activities of the composite immobilized enzyme preparation is easily controlled because the productivity of Hase is high and the DCase catalyzes the irreversible reaction.

The reaction is carried out normally by column method or by suspending the composite immobilized enzyme preparation in a reaction vessel. In the latter case, a batch reaction is usually carried out and the reaction time is about 6 to about 48 hours per batch. By using the composite immobilized enzyme preparation of the present invention, the corresponding D-amino acid can be produced from a 5-substituted hydantoin at a high yield in a one-step reaction. The following examples further illustrate the present invention in detail but are not to be construed to limit the scope thereof.

EXAMPLE 1

Firstly, for preparing an enzyme solution of hydantoinase, Bacillus sp. KNK108 (FERM P-6056) was inoculated to a 250 ml of seed culture medium (meat extract 1.0%, polypeptone 1.0%, yeast extract 0.5% (pH 7.0)) and cultivated at 33° C. for about 25 hours. This seed culture was inoculated to 2.5 liter of a culture medium (meat extract 1.0%, polypeptone 1.0%, yeast extract 0.5%, uracil 0.1%, $MnCl_2$ 20 ppm (pH 7.5)) and cultivated at 33° C. for about 16 hours. The microbial cells were collected by centrifugation and suspended in 50 ml of 20 mM $MnSO_4$ aqueous solution. After adjusting the pH to 8.5, the cells were disrupted by sonication and the residue was removed to obtain a crude enzyme solution of hydantoinase (107 units/ml).

In addition, to prepare an enzyme solution of decarbamylase, E. coli HB101pNT4553 (FERM BP-4368) was cultivated in 20 ml of 2YT medium (Bacto peptone 1.6%, Bacto yeast extract 1.0%, NaCl 0.5%) supplemented with 50 μg/ml ampicillin at 37° C. for about 16 hours. This culture was inoculated to 1.4 liter of 2YT medium in an amount of 1%, and cultivated at 37° C. for about 28 hours. The cells were collected by centrifugation and suspended to 140 ml of 5 mM dithiothreitol solution. After adjusting the pH to 7.0, the cells were disrupted by sonication and the residue was removed to obtain the supernatant as a crude enzyme solution of decarbamylase (36 units/ml).

EXAMPLE 2

By using the crude enzyme solutions obtained in Example 1, immobilization of the enzymes was carried out. Duolite A-568 (Rohm & Haas) as a immobilization support was washed with firstly 1M NaCl and deionized water and then put into the deionized water and the pH was adjusted to 7.5. To 8.4 g of this resin were added 20 ml of the crude enzyme solution of hydantoinase and 11.5 ml of the crude enzyme solution of decarbamylase the pH of both of which had been adjusted to 7.5 and the mixture was stirred at 15° C. for about 20 hours under nitrogen atmosphere. After washing this resin twice with 0.5 mM $MnSO_4$ solution, the resin was suspended in five time volumes of deionized water. After the pH was adjusted to 7.5, the suspension was stirred for 35 minutes with addition of 544 μl of 2.5% glutaraldehyde in two portions. This suspension was treated with 50 mM Tris-HCl (pH 7.5), 5 mM DTT and 1 mM $MnSO_4$ overnight and then the composite immobilized enzyme preparation was collected by filtration (hydantoinase activity 8.2 units (pH 7.5) and decarbamylase activity 9.9 units per 1 g resin).

Then, as controls, resins to which two enzymes were separately immobilized were prepared.

Each of 20 ml of the crude enzyme solution of hydantoinase and 60 ml of the crude enzyme solution of decarbamylase was mixed with each of 4.2 g and 22.0 g of the above immobilization support and the same operations as described above was carried out to obtain each immobilized enzyme resin in which each enzyme was separately immobilized (hydantoinase immobilized enzyme: 24 units/g resin, 2.7 units/g resin (pH7.5), and decarbamylase immobilized enzyme: 37 units/g resin).

EXAMPLE 3

By using the composite immobilized enzyme preparation and control immobilized enzymes containing respective single enzymes obtained in Example 2, the reactions to produce the corresponding D-α-amino acid from a 5-substituted hydantoin were carried out.

After addition of 1g of 5-(p-hydroxyphenyl)hydantoin as the substrate to 100 ml of 0.1 M KPB (pH 7.5), 1 MM $MnSO_4$ and 5 mM DTT, nitrogen gas was sufficiently bubbled in and the reaction conditions were adjusted to 40° C. and pH 7.5. In order to obtain the same enzymatic activities of both enzymes, 0.97 g of the composite immobilized enzyme preparation or 3.0 g of the hydantoinase immobilized enzyme and 0.26 g of the dacarbamylase immobilized enzyme were added. The reaction was carried out with bubbling of nitrogen gas and controlling the reaction pH to 7.5 with 2N $H_2SO_4$ or 6N NaOH. The reaction was carried out for 29 hours with periodical samplings. The amount of p-hydroxyphenylglycine produced at each sampling point was determined by high performance liquid chromatography (Nippon Bunko, Finepack SIL C-18 column).

The results are shown in FIG. 1.

As is seen from FIG. 1, it is found that the reaction can be carried out more efficiently when two enzymes were immobilized simultaneously on the same resin.

EXAMPLE 4

The stability of the enzyme activities was investigated by carrying out the reaction repeatedly with the composite immobilized enzyme preparation. Two grams of 5-(p-hydroxyphenyl)hydantoin was added to 100 ml of 1 mM $MnSO_4$ and 5 mM DTT and pH was adjusted to 7.5. To the mixture was added 8.9 g of the composite immobilized enzyme preparation obtained in Example 2 was added and the reaction was carried out at 40° C. for 23 hours with bubbling of nitrogen gas and controlling the pH to 7.5. After filtering the reaction mixture with suction, another mixture was added to the composite immobilized enzyme according to the same manner as described above and the reaction was carried out. This operation was repeated five times and both enzyme activities were determined at the end of each reaction.

Figure 2:
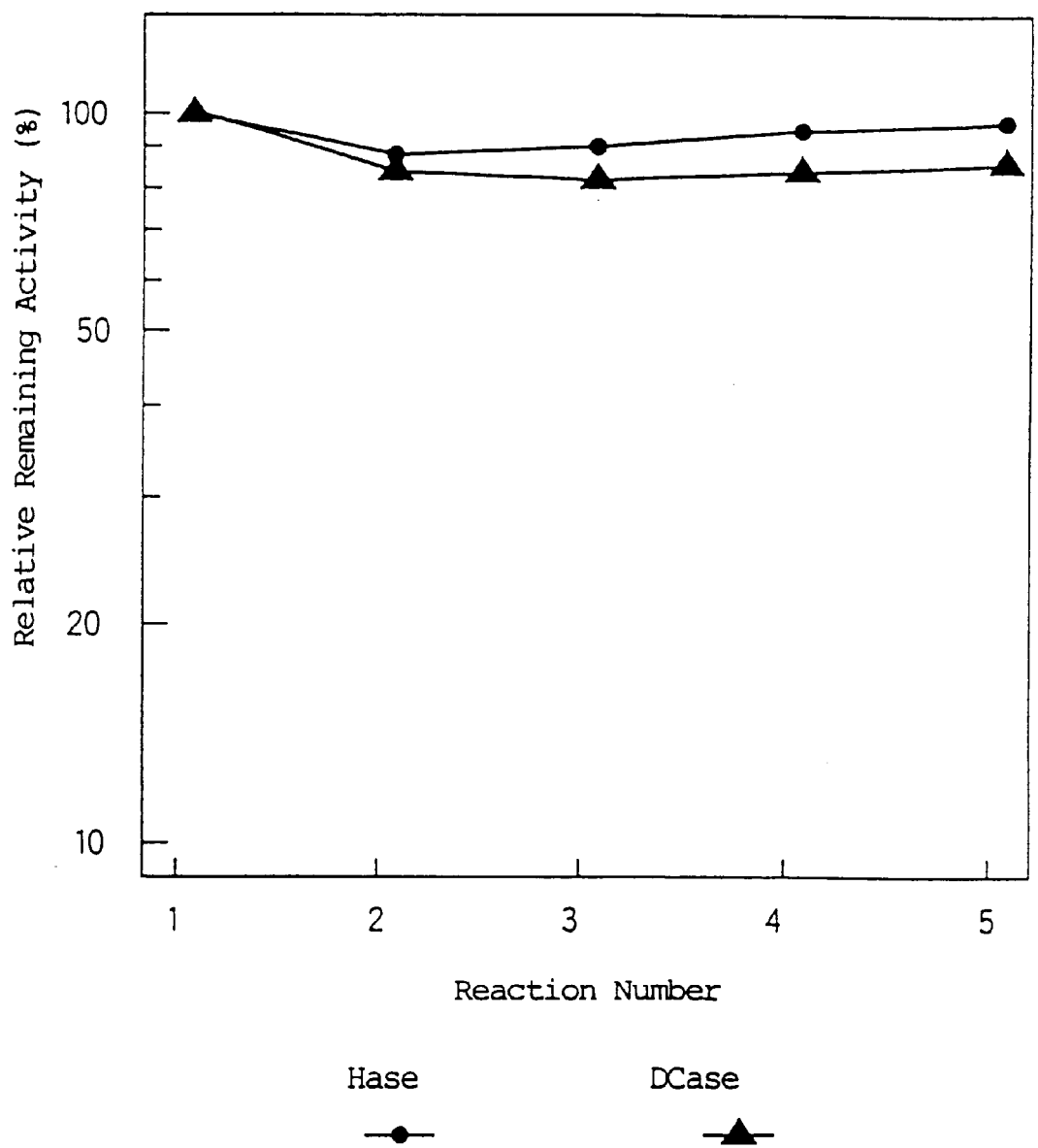
FIG. 2 is a graph illustrating the stability of the enzymes in repeated reactions by using the composite immobilized enzyme preparation in Example 4.

The relative activities to those in the first reaction are shown in FIG. 2.

The decrease in the activities were scarcely observed in these five reactions.

EXAMPLE 5

For preparing an enzyme solution of hydantoinase, *E. coli* HB101pTH104 (FERM BP-4864) containing a hydantoin gene from Bacillus sp. KNK245 (FERM BP-4863) was cultivated in 20 ml of 2YT medium at 37° C. for about 16 hours. This culture was transferred to 1.2 liter of 2YT medium supplemented with 50 μg/ml of ampicillin and 400 ppm of $MnCl_2.4H_2O$ and cultivated for 26 hours at 37° C. The cells were collected by centrifugation and suspended in 80 ml of 1 mM $MnSO_4$ aqueous solution. After adjusting the pH to 8.5 with ammonia water, the cells were disrupted by sonication and the residue was removed by centrifugation. After adjusting the pH of the supernatant to 8.5, heat treatment at 60° C. was carried out for 20 min. The denatured proteins were removed by centrifugation to obtain a crude enzyme solution of hydantoinase (1,100 units/ml).

By using this crude enzyme solution and a crude enzyme solution of decarbamylase prepared according to the same manner as described in Example 1 (240 units/ml), the composite immobilized enzyme preparation was prepared according to the same manner as described in Example 2. By using 30 ml of the crude enzyme solution of decarbamylase and 13 ml of the crude enzyme solution of hydantoinase, the enzymes were immobilized on 29 g of the resin according to the same manner as described in Example 2 (decarbamylase: 45 units, and hydantoinase: 119 units, 44 units (pH 7.5) per 1 g of resin)

As controls, resins on which two enzymes were separately immobilized were used. The decarbamylase immobilized enzyme (43 units/g-resin) was prepared as described in Example 2. The hydantoinase immobilized enzyme was prepared according to the method described in Example 2 by mixing 21.8 g of the resin for immobilization with 60 ml of the crude enzyme solution (177 units/g-resin, 51 units/g (pH 7.5))

EXAMPLE 6

By using 5 g of the composite immobilized enzyme preparation obtained in Example 5, and as immobilized enzymes prepared by immobilizing respective enzymes on different resins, a mixture of 5.6 g of the hydantoinase immobilized enzyme and 5.2 g of the decarbamylase immobilized enzyme obtained in Example 5 (the decarbamylase activity (pH 7.5) was equal to the composite immobilized enzyme preparation and the hydantoinase activity (pH 8.7) was twice as much as the composite immobilized enzyme preparation), the reaction was carried out with 3% substrate according to the method described in Example 3.

Figure 3:
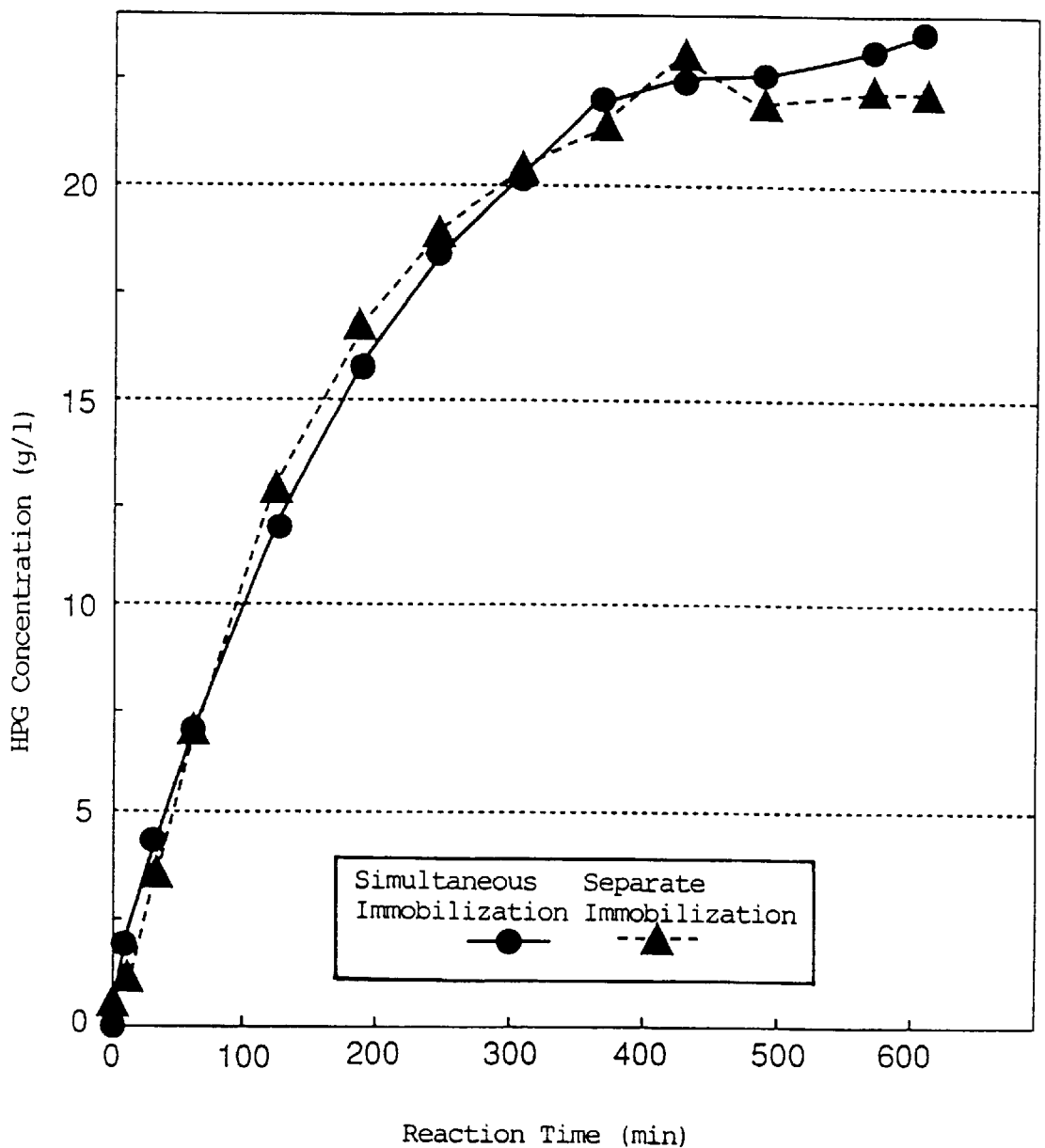
FIG. 3 is a graph illustrating the comparison of the activity of the composite immobilized enzyme preparation with the activity of the mixture of the separately prepared immobilized enzyme preparations (the hydantoinase activity is twice as much as the composite immobilized enzyme preparation) in Example 6.

The results are shown in FIG. 3.

As shown in FIG. 3, the reactivity of the composite immobilized enzyme preparation was similar to the reactivity of the separately immobilized enzymes in spite that the hydantoinase activity was one half of the separately immobilized enzyme. Thus, it has been found that the reaction by the composite immobilized enzyme preparation is more efficient and that the amount of the expensive resin for immobilization can be largely reduced.

EXAMPLE 7

By using each 5 g of the composite immobilized enzyme obtained in Example 5, the effect of the reaction pH was investigated. In three pH levels of 7.0, 7.25 and 7.5, the reactions with 3% substrate were carried out. The times required to convert 99% of the substrate was measured. The times were 5.5, 5.4 and 6.75 hours, respectively. Thus, it have been found that pH 7.0 and 7.25 are advantageous to the reaction.

As described hereinabove, according to the present invention, by using of the composite immobilized enzyme preparation produced by immobilizing the hydantoinase and the decarbamylase simultaneously on the same resin in the production of the corresponding D-α-amino acids from 5-substituted hydantoins, it is possible to carry out the one-step reaction with much simpler operations than two-step reaction and more efficiently than the reaction by the mixture of the two immobilized enzymes obtained by immobilizing these enzymes separately to the different resins.

What is claimed is:

1. A process for the production of a D-aminio acid from the corresponding DL-5-substituted hydantoin which comprises reacting the 5-substituted hydantoin in a concentration of 0. 1 to 30% (w/v) with a composite immobilized enzyme preparation having about 10 to about 20 units/g 5-substituted hydantoin as DCase activity at a pH of about from 6.5 to 8.0, wherein said composite immobilized enzyme preparation comprises an immobilized hydantoinase (Hase) having its optimal pH within an alkaline range and an immobilized D-N-carbamyl-α-amino acid amidohydrolase (DCase) having its optimal pH about neutrality, wherein the ratio of said Hase activity to said DCase activity of said composite immobilized enzyme is about 0.5–1.5 to 1.0 as unit of activity measured at pH 7.5, and wherein said composite immobilized enzyme preparation is prepared by adsorbing said amount of Hase and DCase on and immobilized support in a solution of crude composite enzymes, said solution containing Hase and DCase at a ratio of Hase to DCase of about 1–10 to 1 and containig DCase in a concentration of about 10 to 300 units/ml as a unit of activity measured at pH 7.5 and whereby the said Has a said DCase are immobilized on a simple resin.

2. A process for the production of a D-amino acid according to claim 1, wherein said Hase is that derived from a microorganism belonging to the genus Bacillus.

3. A process for the production of a D-amino acid according to claim 1, wherein said Hase is that derived from Bacillus sp. KNK108 (FERM BP-887), Bacillus sp. KNK245 (FERM BP-4836) or Aerobacter cloacae IAM 1221 (FERM BP-1898).

4. A process for the production of a D-amino acid according to claim 1, wherein said Hase is derived from E. coli HB101pTH104 (FERM BP-4864).

5. A process for the production of a D-amino acid according to claim 1, wherein said DCase is derived from a microorganism selected from the group consisting of Agrobacterium sp. KNK712 (FERM BP-1900), Pseudomonas sp. KNK003A (FERM BP-3181), Pseudomonas sp. KNK505 (FERM B-P-3182), E. coli JM109pAD108 (FERM BP-3184), and E. coli JM109pPD304 (FERM BP-3183).

6. A process for the production of a D-amino acid according to claim 1, wherein said DCase is that derived from a recombinant microorganism selected from the group consisting of E. coli JM109pAD402 (FERM BP-3912), E. coli JM109pAD404 (FERM BP-3913), E. coli JM109pAD406 (FERM BP-3914), E. coli JM109pAD416 (FERM BP-3915), E. coli JM109pAD429 (FERM BP-4035), E. coli JM109pAD421, E. coli JM109pAD422, E. coli JM109pAD423, E. coli JM109pAD424 (FERM BP-4034, E. coli JM109pAD426, E. coli JM109pAD427, E. coli JM109pAD451, E. coli JM109pAD455 (FERM BP-4036), or E. coli JM109pAD4553 (FERM BP-4368), the stability of which is improved by amino acid substitution of the DCase derived from Agrobacterium sp. KNK712 (FERM BP-1900).

7. A process for the production of a D-amino acid according to claim 1, wherein said composite enzyme is produced by cultivating said Hase producer microorganism and said DCase producer microorganism together.

8. A process for the production of D-amino acid according to claim 1, wherein said composite enzyme used for immobilization is prepared by producing said Hase and said DCase simultaneously by cultivating a microorganism selected from the group consisting of Agrobacterium sp. KNK-712 (FERM BP-1900), Rhizobium sp. KNK1415 (FERM BP=4419), Pseudomonas sp. KNK003A (FERM BP-3181), E. coli HB101pPHD301 (FERM BP-4866) and E. coli JM109pAHD101.

9. A process for production of a D-amino acid according to claim 1, wherein said Hase is that derived from a microorganism selected from the group consisting of Agrobacterium radiobacter IFO 13259, Brevibactenun incertum IFO 12145, Microbacternum flavum ATCC 10340, Micrococcus roseus IFO 3764, Pseudomonas striata IFO 12996 and Mycobacterium smegmatis ATCC 607.

10. A composite immobilized enzyme preparation comprising an Hase and a DCase, wherein said Hase and DCase are derived from the same or different microorganisms; an antioxidant; manganese ion and a support carrying said enzymes, land wherein the ratio of said Hase activity to said DCase activity in said composite is about 0.5–1.5 to 1.0 as a unit of activity measured at pH 7.5 and said DCase activity is about 5 to 80 units/g support, wherein said composite immobilized enzyme preparation is prepared by adsorbing said amount of Hase and DCase on an immobilized support in a solution of crude composite enzymes, said solution containing Hase and DCase at a ratio of Hase to DCase of about 1–10 to 1 and containing DCase in a concentration of about 10 to 300 units/ml as a unit of activity measured at pH 7.5 and wherein said Has and said DCase are immobilized on a single resin.

11. A process for the production of a D-amino acid from the corresponding DL-5-substituted hydantoin which comprises reacting the 5-substituted hydantuin in a concentration of 0.1 to 30% (w/v) with a composite immobilized enzyme preparation having about 10 to about 20 units/g 5-substituted hydantoin as DCase activity at a pH of about from 6.5 to 8.0, wherein said composite immobilized enzyme preparation comprises an immobilized hydantoinase (Hasc) having its optimal pH within an alkaline range and an immobilized D-N-carbamyl-α-amino acid amidohydrolase (DCase) having its optimal pH about neutrality, wherein the ratio of said Hase activity to said DCase activity of said composite immobilized enzyme is about 0.5–1.5 to 1.0 as unit of activity measured at pH 7.5, and wherein said Hase and said DCase are immobilized on said support so that both enzymatic reactions occur successively in microspaces of resins.

12. A composite immobilized enzyme preparation comprising an Hase and a DCase, wherein said Hase and DCase are derived from the same or different microorganisms; an antioxidant; manganese ion and a support carrying said enzymes, wherein the ratio of said Hase activity to said DCase activity in said composite is about 0.5–1.5 to 1.0 as a unit of activity measured at pH 7.5 and said DCase activity is about 5 to 80 units/g support, and wherein said Hase and said DCase are immobilized on said support so that both enzymatic are actions occur successively in micro-spaces of resins.

* * * * *